United States Patent
Buras et al.

(10) Patent No.: US 7,706,875 B2
(45) Date of Patent: Apr. 27, 2010

(54) MODULATION OF DRUG EFFECTS BY VAGUS NERVE STIMULATION

(75) Inventors: William R. Buras, Friendswood, TX (US); Jeffrey S. Farroni, Galveston, TX (US)

(73) Assignee: Cyberonics, Inc., Houston, TX (US)

( * ) Notice: Subject to any disclaimer, the term of this patent is extended or adjusted under 35 U.S.C. 154(b) by 323 days.

(21) Appl. No.: 11/698,226

(22) Filed: Jan. 25, 2007

(65) Prior Publication Data

US 2008/0183226 A1    Jul. 31, 2008

(51) Int. Cl.
*A61N 1/00* (2006.01)
(52) U.S. Cl. .......................................................... 607/2
(58) Field of Classification Search .................... 607/2, 607/40, 127, 119; 424/158.1; 623/1.11, 623/1.15, 1.16
See application file for complete search history.

(56) References Cited

U.S. PATENT DOCUMENTS

| | | |
|---|---|---|
| 4,702,254 A | 10/1987 | Zabara |
| 4,714,462 A | 12/1987 | DiDomenico |
| 4,865,048 A | 9/1989 | Eckerson |
| 4,867,164 A | 9/1989 | Zabara |
| 5,025,807 A | 6/1991 | Zabara |
| 5,154,172 A | 10/1992 | Terry, Jr. et al. |
| 5,188,104 A | 2/1993 | Wernicke et al. |
| 5,194,426 A | 3/1993 | Da Vanzo et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |

(Continued)

FOREIGN PATENT DOCUMENTS

WO    94017771    8/1994

(Continued)

OTHER PUBLICATIONS

Bachman, D.,S. et al.; "Effects of Vagal Volleys And Serotonin On Units Of Cingulate Cortex in Monkeys;" Brain Research, vol. 130 (1977). pp. 253-269.

(Continued)

*Primary Examiner*—George Manuel
*Assistant Examiner*—Robert N Wieland
(74) *Attorney, Agent, or Firm*—Conley Rose, P.C.; Timothy L. Scott

(57) ABSTRACT

A method of treating a patient undergoing pharmacotherapy with a selected drug for treatment of a medical disorder is provided which comprises: (a) administering the selected drug to said patient at a first time point, to treat the medical disorder; and (b) applying an electrical signal to a vagus nerve of the patient at a second time point, wherein the signal is selected so as to modulate at least one pharmacologic and/or pharmacokinetic property of the selected drug in the body of the patient. The vagus nerve stimulation (VNS) modulated drug therapy may be performed secondarily to, and in conjunction with, application of a primary VNS therapy to the patient for treatment of the same or a different medical disorder, to enhance treatment of the patient.

23 Claims, 1 Drawing Sheet

U.S. PATENT DOCUMENTS

| | | |
|---|---|---|
| 5,330,507 A | 7/1994 | Schwartz |
| 5,330,515 A | 7/1994 | Rutecki et al. |
| 5,335,657 A | 8/1994 | Terry, Jr. et al. |
| 5,540,730 A | 7/1996 | Terry, Jr. et al. |
| 5,540,734 A | 7/1996 | Zabara |
| 5,558,640 A | 9/1996 | Pfeiler et al. |
| 5,569,186 A | 10/1996 | Lord et al. |
| 5,571,150 A | 11/1996 | Wernicke et al. |
| 5,645,570 A | 7/1997 | Corbucci |
| 5,651,378 A | 7/1997 | Matheny et al. |
| 5,662,689 A | 9/1997 | Elsberry et al. |
| 5,665,706 A | 9/1997 | DaVanzo et al. |
| 5,690,681 A | 11/1997 | Geddes et al. |
| 5,700,282 A | 12/1997 | Zabara |
| 5,707,400 A | 1/1998 | Terry, Jr. et al. |
| 5,893,881 A | 4/1999 | Elsberry et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,935,099 A | 8/1999 | Peterson et al. |
| 5,978,702 A | 11/1999 | Ward et al. |
| 5,995,868 A | 11/1999 | Osorio et al. |
| 5,995,872 A | 11/1999 | Bourgeois |
| 6,024,539 A | 2/2000 | Blomquist |
| 6,083,249 A | 7/2000 | Familoni |
| 6,091,992 A | 7/2000 | Bourgeois et al. |
| 6,092,528 A | 7/2000 | Edwards |
| 6,097,984 A | 8/2000 | Douglas |
| 6,104,955 A | 8/2000 | Bourgeois |
| 6,104,956 A | 8/2000 | Naritoku et al. |
| 6,109,269 A | 8/2000 | Rise et al. |
| 6,152,953 A | 11/2000 | Hipskind |
| 6,161,044 A | 12/2000 | Silverstone |
| 6,176,242 B1 | 1/2001 | Rise |
| 6,178,349 B1 | 1/2001 | Kieval |
| 6,205,359 B1 | 3/2001 | Boveja |
| 6,208,902 B1 | 3/2001 | Boveja |
| 6,216,039 B1 | 4/2001 | Bourgeois |
| 6,241,704 B1 | 6/2001 | Peterson et al. |
| 6,269,270 B1 | 7/2001 | Boveja |
| 6,270,455 B1 | 8/2001 | Brown |
| 6,308,104 B1 | 10/2001 | Taylor et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,366,814 B1 | 4/2002 | Boveja et al. |
| 6,381,499 B1 | 4/2002 | Taylor et al. |
| 6,429,217 B1 | 8/2002 | Puskas |
| 6,438,423 B1 | 8/2002 | Rezai et al. |
| 6,449,507 B1 | 9/2002 | Hill et al. |
| 6,449,512 B1 | 9/2002 | Boveja |
| 6,459,936 B2 | 10/2002 | Fischell et al. |
| 6,468,263 B1 | 10/2002 | Fischell et al. |
| 6,473,644 B1 | 10/2002 | Terry, Jr. et al. |
| 6,477,418 B2 | 11/2002 | Plicchi et al. |
| 6,505,074 B2 | 1/2003 | Boveja et al. |
| 6,532,388 B1 | 3/2003 | Hill et al. |
| 6,535,764 B2 | 3/2003 | Imran et al. |
| 6,542,776 B1 | 4/2003 | Gordon |
| 6,556,868 B2 | 4/2003 | Naritoku et al. |
| 6,564,102 B1 | 5/2003 | Boveja |
| 6,571,125 B2 | 5/2003 | Thompson |
| 6,587,719 B1 | 7/2003 | Barrett et al. |
| 6,587,726 B2 | 7/2003 | Lurie et al. |
| 6,587,727 B2 | 7/2003 | Osorio et al. |
| 6,591,137 B1 | 7/2003 | Fischell et al. |
| 6,591,138 B1 | 7/2003 | Fischell et al. |
| 6,600,953 B2 | 7/2003 | Flesler et al. |
| 6,606,523 B1 | 8/2003 | Jenkins |
| 6,609,025 B2 | 8/2003 | Barrett |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry et al. |
| 6,622,047 B2 | 9/2003 | Barrett et al. |
| 6,628,987 B1 | 9/2003 | Hill et al. |
| 6,650,943 B1 | 11/2003 | Whitehurst et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,690,973 B2 | 2/2004 | Hill et al. |
| 6,721,603 B2 | 4/2004 | Zabara et al. |
| 6,754,536 B2 | 6/2004 | Swoyer et al. |
| 6,760,626 B1 | 7/2004 | Boveja |
| 6,788,970 B1 | 9/2004 | Park et al. |
| 6,788,975 B1 | 9/2004 | Whitehurst et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,889,076 B2 | 5/2005 | Cigaina |
| 6,895,278 B1 | 5/2005 | Gordon |
| 6,920,357 B2 | 7/2005 | Osorio et al. |
| 6,961,618 B2 | 11/2005 | Osorio et al. |
| 7,167,750 B2 | 1/2007 | Knudson et al. |
| 2003/0208212 A1 | 11/2003 | Cigaina |
| 2004/0167583 A1 | 8/2004 | Knudson et al. |
| 2004/0172085 A1 | 9/2004 | Knudson et al. |
| 2004/0172088 A1 | 9/2004 | Knudson et al. |
| 2004/0176812 A1 | 9/2004 | Knudson et al. |
| 2005/0038484 A1 | 2/2005 | Knudson et al. |
| 2005/0107753 A1 | 5/2005 | Rezai et al. |
| 2005/0131485 A1 | 6/2005 | Knudson et al. |
| 2005/0131486 A1 | 6/2005 | Boveja et al. |
| 2006/0041222 A1 | 2/2006 | Dewing et al. |
| 2006/0041287 A1 | 2/2006 | Dewing et al. |
| 2006/0106431 A1 | 5/2006 | Wyler et al. |
| 2006/0111644 A1 | 5/2006 | Guttag et al. |
| 2006/0167497 A1 | 7/2006 | Armstrong et al. |
| 2006/0247722 A1* | 11/2006 | Maschino et al. ............. 607/40 |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2008/0275514 A1* | 11/2008 | Ben-David et al. ............. 607/2 |

FOREIGN PATENT DOCUMENTS

| | | |
|---|---|---|
| WO | 05007120 | 1/2005 |
| WO | 05007232 | 1/2005 |

OTHER PUBLICATIONS

Borovikova, L.V., et al.; " Vagus Nerve Stimulation Attenuates the Systemic Inflammatory Response to Endotoxin;" Letters to Nature; vol. 405; (May 2000); pp. 458-462.

Chandler, Margaret J. et al., "Vagal, Sympathetic and Somatic Sensory Inputs to Upper Cervical (CI -C3) Spinothalamic Tract Neurons in Monkeys;" Journal of Neurophysiology, vol. 76 No. 4, pp. 2555-2567 (Oct. 1996).

Clark, K.B., et al.; "Enhanced Recognition Memory Following Vagus Nerve Stimulation in Human Subjects;" Nature Neuroscience, vol. 2, No. 1, (Jan. 1999) pp. 93-98.

Grundy et al., "Sensory Afferents From the Gastrointestinal Tract" Chapter 16, Handbook of Physiology of Abdominal Vagal Afferents, Chapter 12, CRC Press, New York, NY, 1992.

Hallowitz et al., "Effects of Vagal Volleys on Units of Intralaminar and Juxtalaminar Thalamic Nuclei in Monkeys;" Brain Research, vol. 130 (1977), pp. 271-286.

Kriwanek, S., et al.; "Therapeutic Failures After Gastric Bypass Operations Pot Morbid Obesity," Langenbecks Archiv Fur Chirurgie, 38(2): 70-74, 1995.

Leibowitz, S.F., "Central Physiological Determinants of Eating Behavior and Weight" Eating Disorders and Obesity: A Comprehensive Handbook, Ch. 1, Brownell and Fairburn. Ed.. The Guilford Press, 1995.

Ritter, S., et al.; "Participation of Vagal Sensory Neurons in Putative Satiety Signals from the Upper Gastroinstestinal Tract" Neuroanatomy and Physiology of Abdominal Vagal Afferents, Ch. 10 (1992); pp. 222-248.

Smith, D.C., et al.; "Electrical Stimulation of the Vagus Nerve Enhances Cognitive and Motor Recovery Following Moderate Fluid Percussion Injury in the Rat" Journal of Neurotrauma, vol. 22, No. 12, (2005) pp. 1485-1502.

Smith, D.C., et al.; "Recovery of Function After Vagus Nerve Stimulation Initiated 24 Hours After Fluid Percussion Brain Injury" Journal of Neurotrauma vol. 23, No. 10 (2006) pp. 1549-1560.

Tatum, W.O., et al.; "Vagus Nerve Stimulation and Drug Reduction" Neurology, vol. 56, No. 4 (Feb. 2001) pp. 561-563.

Terry et al.; "The Implantable Neurocybernetic Prosthesis System", Pacing and Clinical Electrophysiology, vol. 14, No. 1 (Jan. 1991), pp. 86-93.

* cited by examiner

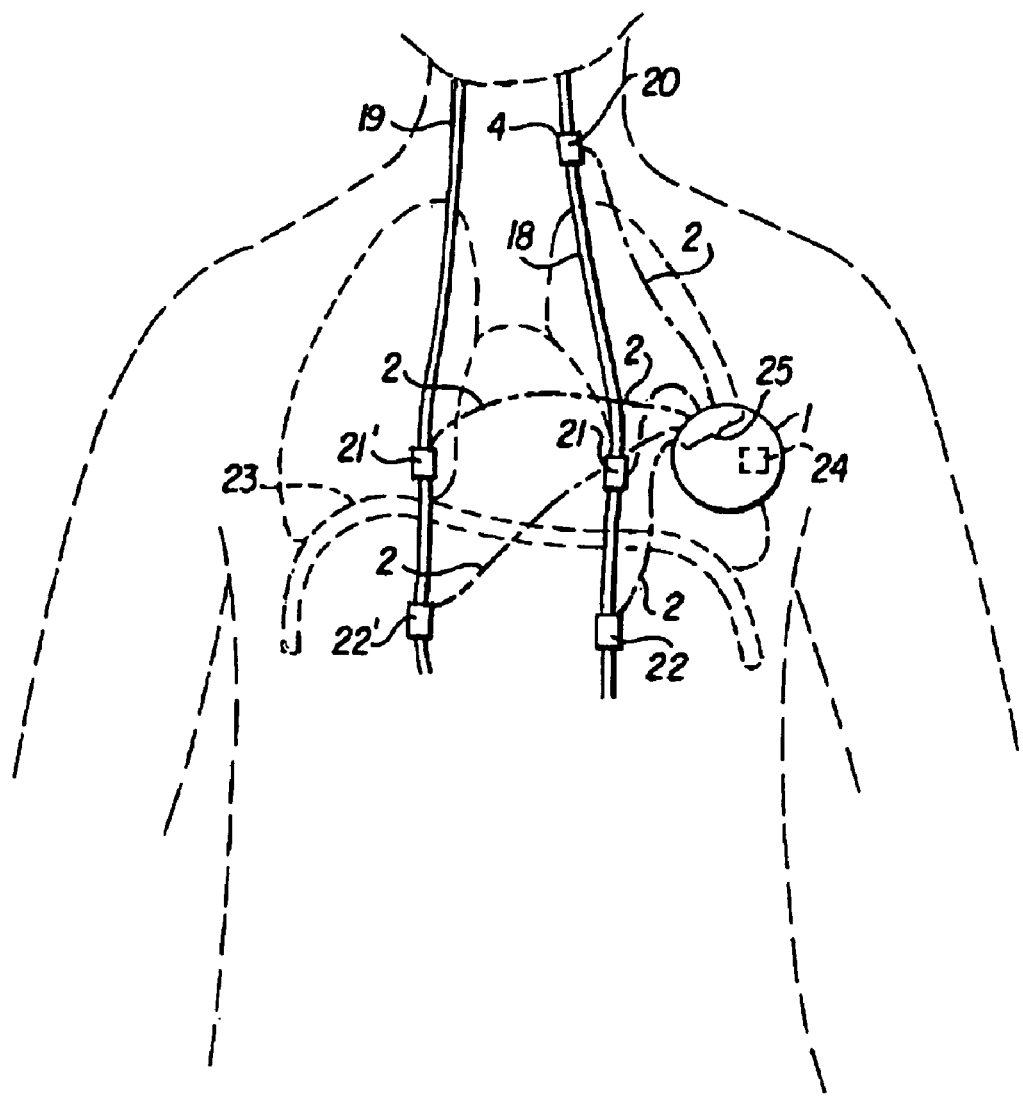

MODULATION OF DRUG EFFECTS BY VAGUS NERVE STIMULATION

BACKGROUND

1. Technical Field

The present invention generally relates to improving desired effects of a drug taken by a patient, and minimizing undesired effects of the drug, such as by modulation of drug efficacy, side effect profile and therapeutic index of the drug, and more particularly to methods and apparatus employing vagus nerve stimulation to improve the efficacy, side effect profile, and/or therapeutic index of a drug that is administered to an individual for therapeutic purposes.

2. Description of Related Art

The relative safety of a drug is typically indicated by its "therapeutic index," which is the ratio of the median lethal dose ($LD_{50}$) to the median medically effective dose ($MED_{50}$). The therapeutic index of a given drug is desirably a large number (e.g., 10 or more), indicating that the range of therapeutically recommended dosages is much lower than the potentially lethal dosage range. Drugs identified as having a high risk of being involved in a clinically significant adverse effect frequently have a narrow therapeutic index, a very steep dose-response curve or potent pharmacologic effects. A toxic dose of such drugs may be only slightly above the therapeutic dose, in which case even a slight increase in the dose may produce a large increase in serum drug levels and an adverse clinical effect. Conversely, a slight decrease in the plasma level of drugs with a steep dose-response curve may result in a significant loss of therapeutic effect.

Drug interactions and adverse side effects have an enormous impact on treatment and quality of life. An adverse drug reaction can be defined as an unexpected diminished or enhanced pharmacologic activity or toxicity of a drug when used alone, or any noxious response to a drug that occurs at doses used in humans for prophylaxis, diagnosis, or therapy. One approach to mitigating the drug dose-limiting toxicity problem is to administer the primary drug at a lower than optimum dose, together with administration of a second drug with non-overlapping toxicity. Ways to improve the efficacy and therapeutic index of therapeutically useful drugs are sought.

Primary determinants of drug efficacy and therapeutic index are the pharmacologic properties of the drug and also its pharmacokinetic properties, such as absorption, clearance, plasma binding, solubility and volume of distribution, among others, as well as the time periods in which such properties occur. A marked shift in serum drug levels can significantly alter clinical response. Pharmacokinetic properties influence the disposition of a drug in the body and may also affect the effects of one drug on the absorption, distribution, metabolism and/or excretion of other drugs in a person's body.

It is well established from neuroanatomical studies that the vagus nerve has afferent projections into the hypothalamus, brainstem and limbic areas of the brain, which has been corroborated by numerous functional imaging studies. Those regions regulate homeostatic mechanisms such as salt and water balance, digestion (stomach pH) and excretion. Consequently, the pharmacokinetics (i e., absorption, distribution, localization in tissues, biotransformation, excretion, mode of action (MOA), concentration, effect) of an ingested drug is also affected by vagus nerve activity, including absorption, distribution and elimination of the drug. The vagus nerve also has direct efferent projections on target organs involved in homeostasis. For instance, the knowledge of mechanisms involved in osmotic regulation across the intestinal epithelium has been substantially refined over the past two decades. It is known that extrinsic as well as intrinsic innervation of the gut plays a major role in regulating the intestinal absorption of numerous compounds routinely used for the treatment of common diseases is profoundly limited by their physiochemical characteristics. It has also been shown that vagal afferent pathways are active in the inhibition of gastric emptying induced by acid and different food ingredients.

Therapeutic use of VNS has been described for disorders such as medically refractory seizures, which are seizures that occur despite treatment with therapeutic levels of antiepileptic drugs. VNS has also been approved for treatment of seizures in individuals that cannot be treated with therapeutic levels of antiepileptic drugs due to intolerable adverse side effects of the drugs, and for depression in patients who have failed to achieve significant benefits from drug therapies. VNS has also been described and continues to be investigated for treatment of eating disorders such as bulimia, anorexia and obesity, and for traumatic brain injury including stroke.

SUMMARY

Ways to improve the efficacy, therapeutic index and other desirable properties of therapeutically useful drugs are provided in accordance with certain embodiments of the present invention. In accordance with certain embodiments, a method of treating a patient undergoing pharmacotherapy with a selected drug for treatment of a medical disorder is provided which comprises: (a) administering the selected drug to the patient at a first time point to treat the medical disorder; and (b) applying a first electrical signal to a vagus nerve of the patient at a second time point, wherein the first electrical signal is selected so as to modulate at least one pharmacologic and/or pharmacokinetic property of the selected drug in the body of the patient, and wherein said second time point is selected from the group consisting of a selected time before said first time point, a selected time after said first time point, and a selected time in the patient's circadian rhythm after said first time point.

Some embodiments of the above-described method administer a therapeutically effective reduced dosage of the drug compared to the dosage that would be administered to the patient in the absence of applying the first electrical signal to the vagus nerve to achieve a similar therapeutic effect. In certain embodiments, modulating the at least one pharmacologic and/or pharmacokinetic property of the drug comprises increasing the therapeutic index of the drug. In certain embodiments, the first signal is applied to a vagus nerve site in the cervical region of the patient. In certain embodiments, the first signal is applied to at least one site on the vagus nerve in the supra-diaphragmatic thoracic region of the patient or in the sub-diaphragmatic abdominal region of the patient.

In some embodiments of an above-described method, the drug is administered to the patient immediately before applying the first electrical signal to the vagus nerve. In some embodiments, the second time point is a predetermined interval of time after the first time point.

In certain embodiments, the drug is administered to the patient chronically, and the first electrical signal comprises repeatedly applying the first electrical signal at a predetermined series of time intervals after the first time point.

In certain embodiments, the method further includes applying a second electrical signal, which is different from the first electrical signal, to a vagus nerve of the patient. The second electrical signal is selected so as to treat a medical condition of a patient independent of the effects of the drug.

In certain embodiments, a pharmacologic and/or pharmacokinetic property comprises the rate of intestinal absorption of the selected drug, or a biologically active metabolite thereof. In certain embodiments, a pharmacologic and/or pharmacokinetic property comprises plasma binding of the selected drug, solubility of the drug in a body fluid, volume of distribution of the drug, or clearance of the drug.

In certain embodiments, application of the first electrical signal to a vagus nerve causes modulation of the hypothalamus area of the patient's brain. In some embodiments, application of the first electrical signal to a vagus nerve causes modulation of the brainstem area of the patient's brain. In some embodiments, application of the first electrical signal to a vagus nerve causes modulation of the function of an organ selected from the group consisting of the stomach, the pancreas, the liver, the lungs, the intestines, and the kidneys.

In certain embodiments, applying the first electrical signal to the vagus nerve comprises applying a first electrical signal to a main branch of the left or right vagus nerves, or to a branch of the vagus nerve connecting a main branch of the vagus nerve to an organ selected from the group consisting of the stomach, the pancreas, the liver, the lungs, the intestines and the kidneys.

In certain embodiments, applying the first electrical signal to the vagus nerve comprises applying the first electrical signal to an electrically conductive tissue adjacent to the vagus nerve to indirectly apply the first electrical signal to the vagus nerve.

Also provided in accordance with certain embodiments is a method of enhancing treatment of a patient undergoing pharmacotherapy with a predetermined dosage of a selected drug for treatment of a medical disorder. This embodiment includes (a) administering a first predetermined dosage of the drug to the patient; (b) applying a first electrical signal to at least one site on a left or right vagus nerve of the patient, wherein the first electrical signal is selected so as to modulate at least one pharmacologic and/or pharmacokinetic property of the selected drug in the body of the patient; (c) determining from the resulting modulation of the at least one property an increase or decrease in the efficacy of the drug; and (d) decreasing the drug dosage to enhance treatment of the patient for the disorder if the resulting modulation increases the efficacy of the drug.

Certain embodiments also provide a method of enhancing treatment of a patient undergoing therapeutic vagus nerve stimulation for a medical disorder. This embodiment includes (a) applying a first electrical signal to a site on a vagus nerve of the patient, wherein the first electrical signal is selected so as to therapeutically treat the medical disorder; (b) administering a drug therapy to the patient for the same or a different medical disorder; and (c) applying a second electrical signal to a site on a vagus nerve to enhance the drug therapy. In some embodiments, the second electrical signal is applied to a different site on a vagus nerve than the first electrical signal. In some embodiments, the second signal is applied during off-times of the first signal. In some embodiments, enhancing a drug therapy comprises enhancing at least one property selected from the group consisting of enhancing bioavailability, efficacy and safety of the drug.

In certain embodiments, the first electrical signal, the drug, and the second electrical signal are selected to synergistically enhance treatment of the patient's medical disorder.

These and other embodiments, features and advantages will be apparent from the following drawing and the detailed description.

BRIEF DESCRIPTION OF THE DRAWING

The FIGURE is a simplified partial front view of a patient's body (in phantom lines) showing possible sites on the left and right vagus nerve for electrode attachment in the cervical, thoracic and abdominal areas of the body, and coupling to an implanted stimulus generator.

DETAILED DESCRIPTION

As used herein, "stimulation" or "stimulation signal" refers to the application of an electrical, mechanical, magnetic, electromagnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electromagnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a disorder by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the target neural structure, while the effects of that signal, if any, on the electrical activity of the target neural structure and/or other neural structures (such as the brain) enervated by the target structure are properly referred to as "modulation." The effect of delivery of the stimulation signal to the neural tissue may be excitatory or inhibitory and may potentiate acute and/or long-term changes in neuronal activity. For example, the "modulating" effect of the stimulation signal to the neural tissue may comprise one more of the following effects: (a) changes in neural tissue to initiate an action potential (afferent and/or efferent action potentials); (b) inhibition of conduction of action potentials (whether endogenous or exogenously induced) or blocking the conduction of action potentials (hyperpolarizing or collision blocking), (c) affecting changes in neurotransmitter/neuromodulator release or uptake, and (d) changes in neuroplasticity or neurogenesis of brain tissue.

Thus, electrical neurostimulation or modulation of a neural structure refers to the application of an exogenous electrical signal (as opposed to mechanical, chemical, photonic, or another mode of signal delivery) to the neural structure. Electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body. In another alternative embodiment, the signal may be generated by an external pulse generator outside the patient's body, coupled by an RF or wireless link to an implanted electrode.

Generally, neurostimulation signals to perform neuromodulation are delivered by the implantable device via one or more leads. The leads generally terminate into electrodes, which are affixed onto a tissue in the patient's body. A number of leads may project from an implantable device onto various portions of a patient's body. For example, a number of electrodes may be attached to various points of a nerve or other tissue inside a human body for delivery of neurostimulation.

Certain terms are used throughout the following description and claims refer to particular system components. As one skilled in the art will appreciate, components may be referred to by different names. This document does not intend to distinguish between components that differ in name but not function. In the following discussion and in the claims, the terms "including" and "including" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, electric (e.g., as in capacitive) or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

Neurostimulation has frequently been delivered as a pulsed electrical signal in discrete stimulation periods known as pulse bursts, which constitute a series of controlled pulses having a programmed, non-random and constant current (e.g., 1 milliamp), a programmed frequency (e.g., 30 Hz), a programmed pulse width (e.g., 500 microseconds), a programmed current polarity, e.g., current flow from electrode 226 to electrode 228, for a period of time, e.g., 30 seconds. The period of time in which a stimulation signal is delivered (30 seconds in the example) is referred to herein as on-time. Bursts are typically separated from adjacent bursts by another period of time, e.g. 5 minutes in which no signal is applied to the neural target. The period of time between delivery of stimulation signals (5 minutes in the example) is referred to herein as off-time. Ramping of the current or voltage over the first few seconds or pulses of a pulse burst is sometimes employed to avoid pain which can be associated with having the initial pulses of a burst at full amplitude. The frequency, which is determined by a plurality of similar adjacent pulse-to-pulse intervals, may be constant or may vary. The pulse-to-pulse interval is referred to herein as a pulse period, and is distinct from frequency in that a pulse period is independent from pulse to pulse, whereas a frequency, by definition, requires a plurality of similar adjacent pulse periods. More recently, it has been proposed to randomly vary one or more parameters defining a pulsed electrical signal used for neurostimulation. Where the timing of pulses is random or nonuniform, it may be more useful to refer to "pulse period" instead of frequency, because pulse periods may vary randomly within a predetermined range, or nonrandomly according to a predetermined program.

Therapeutic vagus nerve stimulation (VNS) has the potential to enhance drug efficacy and increase the therapeutic index of a selected drug in patients undergoing treatment with the selected drug for a given disorder. As used herein, "unilateral stimulation" refers to the application of an electrical signal to either the left main branch or the right main branch of the vagus nerve, but not both. The signal may be applied in the cervical, thoracic, or abdominal regions. "Bilateral stimulation" as used herein, refers to application of an electrical signal to both the left and the right main branches of the vagus nerve. In alternative embodiments, electrical signals may be applied to specific branches of the vagus nerve, e.g., the hepatic branch, to affect specific target organs or body areas. Some of the disorders that will potentially benefit from the disclosed methods include, but are not limited to epilepsy; movement disorders such as Parkinson's disease; neuropsychiatric disorders such as depression, schizophrenia, borderline personality disorder, autism and attention deficit/hyperactivity disorder (ADHD); eating disorders such as bulimia, anorexia, obesity; endocrine disorders such as diabetes; hypertension; pain; migraine headache; traumatic brain injury and stroke; sleeping disorders; and chronic or intractable pain. The route of administration of the drug may vary, depending on the particular disorder being treated, and also on such factors as ease of administration, effects of the drug on local tissue, solubility of the drug, ionic characteristics of the drug, size of the drug molecule, and on how the drug is metabolized by the body. With oral administration, the drug is typically absorbed through the walls of the stomach and intestines and enters the bloodstream. Slower and more sustained rates of delivery usually result from subcutaneous, transdermal, and intramuscular administration. Inhalation of drug vapors or injection of drugs directly into the bloodstream (intra-arterial or intravenous administration) tends to produce a more rapid onset of drug effects. The duration of a drug's effects are determined primarily by the rate at which the drug is metabolized. Usually, enzymes in the digestive tract or the liver are responsible for converting drugs into inactive forms. The resulting metabolites are then removed from the body as waste products, via the bowel, urine, skin, or by exhalation from the lungs.

It is projected that VNS will be useful for therapeutically influencing pharmacokinetic and pharmacodynamic properties of exogenous chemicals prescribed for the treatment of a variety of chronic disorders. A selected electrical signal, applied directly or indirectly to one or more sites on the vagus nerve, may induce afferent action potentials to modulate brain regions involved in homeostatic regulatory mechanisms, e.g., hypothalamus, limbic and brainstem structures, by modulation of neural projections to/from those regions, such as biogenic amines, cholinergic, inhibitory ligand-gated ion channels, and others. Alternatively or additionally, a selected electrical signal applied to the vagus nerve may generate efferent action potentials to modulate the function of one or more target organ. Stimulation (or modulation) of target organs such as the brain, stomach, liver, intestine and kidney, potentially modulates homeostatic mechanisms including salt and water balance, digestion (e.g., stomach pH) and excretion, resulting in an altered pharmacologic profile of drugs processed by the target organ. By modulation of such properties as drug absorption, clearance, plasma binding, solubility and volume of distribution, via specific electrical signals applied at particular sites on the vagus nerve, VNS will potentially increase efficacy, tolerability and the safety profile of pharmacotherapy for chronically treated disorders. As used herein when referring to a drug's properties, the terms "modulation," "modulates," "modulating," and variations thereof, refer to increasing or decreasing a characteristic or property associated with the drug, such as one or more pharmacokinetic or pharmacologic property of the drug.

Operation.

Referring to FIG. 1, an exemplary protocol for improving the efficacy and safety of a selected drug in a patient undergoing therapeutic drug treatment for a predetermined disorder utilizes an implantable electrical signal generator 1 for selectively applying, when activated, a therapeutic electrical signal to at least one electrode of a lead assembly 2 electrically coupled to the signal generator 1. Electrical signal generator 1 is surgically implanted at an appropriate site in the patient's body using conventional surgical techniques. For instance, generator 1 may be implanted in a pocket formed just below either the epidermal layer or a muscular layer in or near the patient's chest. Alternatively, generator 1 may be implanted in the abdominal region (not shown), via a left laparotomy incision, for example, or other conventional surgical technique.

A lead assembly 2 having one or more conventional leads electrically connected to generator 1 terminate at one or more electrodes 4, at one or more sites 20, 21, 21', 22 and 22'. The electrodes and associated leads are implanted in an electrically coupled relation to the left and/or right vagus nerve 18, 19 at one or more sites of the cervical region, thoracic region and abdominal region. When the electrodes are implanted in the abdominal region, the electrodes may be electrically coupled to the vagus nerve in the supra-or sub-diaphragmatic area ranging from about 2-3 inches (5.16 cm) above to about 2-3 inches (5.16 cm) below the diaphragm. The cervical site requires the least invasive surgery; however, it may be desirable in many cases to implant one or more electrodes at supra- or subdiaphragmatic sites, either unilaterally or bilaterally. The nerve electrodes may be equipped with tethers for maintaining each electrode in place without undue stress on the site at which the electrode is coupled to the nerve. In one embodiment, electrical contact is provided by direct contact with the nerve.

After the selected area(s) of the left and/or right vagus nerve is/are coupled to the electrode(s), and the respective lead(s) is/are connected to the implanted (or external) signal generator, the signal generator is operates to produce the programmed electrical signal until interrupted by the patient (in some cases) or a healthcare provider (i.e., a physician reprogramming the generator). A generally suitable form of electrical signal generator is disclosed in U.S. Pat. No. 5,154, 172, and a commercial embodiment of a suitable stimulation generator is produced by Cyberonics, Inc. of Houston, Tex., as the Model 102 or Model 102R generator. Certain parameters defining the electrical signal are programmable, preferably by means of an external programmer (not shown) in a conventional manner for implantable electrical medical devices.

Unilateral Stimulation. In one embodiment of the present invention, an electrical signal may be provided, using an electrical signal generator as described above, unilaterally to the left or the right vagus nerve. The above-mentioned Model 102 and 102R generators available from Cyberonics, Inc. have one or two receptacles for receiving the lead assembly 2. In alternative embodiments, the electrical signal may be generated by an external neurostimulator that is inductively coupled to an implanted lead having an electrode coupled to either the left or the right vagus nerve. In either case, the signal may be applied continuously, periodically or intermittently, with automatic or manual activation of the generator 1, depending on the electrical signal program. The programmable electronics package 24 inside generator 1 is indicated schematically in FIG. 1. Using the Cyberonics Model 102, or another suitable pulse generator, and associated software, it is possible to program the electrical signal parameters defining the signal, including its current, frequency or pulse period, pulse width, on-time, off-time and/or duty cycle.

In one exemplary embodiment, the electrical signal generator 1 may be programmed to provide a pulsed electrical signal having a current ranging from about 0.1 to about 10 ma, more preferably from about 0.5 to about 4.0 ma, although practical upper limits on current may be determined by patient discomfort or pain; the frequency may range from about 0.25 to about 1000 Hz, more preferably from about 1 Hz to about 50 Hz; the pulse width may range from about 1.0 microsecond (μs) to about 2.0 milliseconds (ms); the on-time may range from 1.0 second to a continuous signal, but more preferably will range from about 10 seconds to about 300 seconds, with 30 seconds being a common setting; the off-time may range from 0 seconds (for continuous signals), to 24 hours, more preferably from about 10 seconds to about 1 hour. Where random signals are employed the pulse period may be programmed to vary randomly from a range within the range of from 1 millisecond to 1 second, more preferably from a range within the range of 1 millisecond to about 100 milliseconds. Thus, a suitable therapeutic electrical signal might comprise a pulsed signal having a current of 1.0 ma, a frequency of 30 Hz, a pulse width of 500 μs, an on-time of 30 seconds, and an off-time of 300 seconds. It will be understood, however, that the optimum value of the parameters of the stimulating signal will differ, depending on the selected drug and how it is metabolized, and the selected organ in the body (e.g., stomach, liver, kidney) whose processing of the drug is to be affected. Depending upon factors such as what drug is being provided to the patient, the patient's condition, and the target organ whose processing of the drug is to be affected, the magnitude of the electrical signal that will be efve for modulating the drug's pharmacokinetic and/or pharmacology properties may be less, approximately the same as, or greater than therapeutic VNS signals typically employed today for treatment of epilepsy, depression, obesity, and other disorders.

Bilateral Stimulation. In a variation of the above-described unilateral stimulation protocol, one or more stimulus generator 1 comprises at least two electrodes to apply an electrical signal to both the right vagus and the left vagus, to provide bilateral stimulation.

In addition to unilateral and bilateral stimulation of the left and/or right branches of the main vagus nerve, embodiments of the invention may further comprise stimulation of particular branches of the vagus nerve to modulate the electrical activity of a target organ to affect one or more pharmacokinetic properties of the drug in the patient's body. In one embodiment, the electrical signal may be applied to the hepatic branch of the vagus nerve to affect drug metabolism of the liver. It should further be noted, regardless off whether the stimulation is applied unilaterally, bilaterally, or to specific branches of the vagus nerve, that the signal will usually be applied intermittently according to the programmed on-time and off-time. Nevertheless, continuous application of the electrical pulse signal may also be effective in providing the desired modulation of a selected drug's pharmacologic and/or pharmacokinetic properties. In addition, some embodiments may involve different electrical signals to be applied at different times to enhance therapeutic effectiveness for the drug. For example, a first electrical signal may be applied immediately upon administration of the drug for a predetermined period, e.g., 2 hours. This protocol may be used, for example, to speed absorption of the drug into the patient's bloodstream. At the conclusion of the first protocol, a second protocol may be applied for a different time period, for example six hours. The second signal may be used for a different purpose, for example to speed processing of the drug by the liver. The second signal may be followed by a third electrical signal for still another purpose, for example, to improve elimination of undesirable metabolic byproducts from the patient's body. Accordingly, specific electrical signals may be used for specific pharmacokinetic purposes.

In some cases, the implanted device is programmed to provide stimulation according to the time of day (e.g., differently during daytime and nighttime hours), or otherwise according to the circadian rhythm of the patient. In addition, the electrical signal applied to the vagus nerve may be structured so as to generate afferent action potentials for modulation of the brain, efferent action potentials to modulate a target organ other than the brain, or both.

The use of implanted electrical signal for performing vagus nerve stimulation is generally preferred over external or partially external systems because it allows the patient to be completely ambulatory, so that normal daily routine activities including on the job performance is unaffected. In some cases, however, it may be preferable to instead administer VNS stimulation for modulation of drug effects using one or more external stimulus generators. For instance, when treatment is desired on an out-patient basis only, or for hospitalized or non-ambulatory patients.

In still another embodiment of the invention involving stimulation of particular branches of the left or right vagus nerves to affect a selected organ (e.g., stomach, liver, intestine, kidney), a "paddle" type of electrode may be preferred over a helical type electrode, for attaching to the surface of the chosen organ for direct stimulation, or for attaching to nearby tissue if indirect stimulation is desired. For instance, an electrode may be placed within about 1 inch of a target tissue innervated by a branch of the vagus nerve, and the electrical signal may be indirectly applied to the vagus nerve branch to affect the target tissue.

Stimulation Algorithm. A suitable stimulation algorithm for use with a selected drug treatment therapy is generally determined by spectral optimization, in which the various parameters, or specific parameters, of the signal are increased in steps from a designated minimum value or starting value over intervals of several days or weeks, and the patient's response and/or drug levels in the body is/are monitored. In some instances, application of the stimulation spectrum is done in concert with functional brain imaging. In some cases, the level of electrical current of the stimulus signal that will be effective for modulating a selected drug's pharmacokinetic and/or pharmacology properties may be less than that typically employed today for therapeutic VNS treatment of epilepsy, depression, obesity, and other disorders (i.e., subthreshold for VNS treatment of a predetermined primary disorder). In such cases, the use of VNS for improving drug efficacy and therapeutic index can be employed in combination with therapeutic VNS treatment of a patient's primary disorder such as epilepsy, neuropsychiatric disorders, eating disorders, and others that are amenable to VNS therapy. For instance, the drug modulation routine may be applied as a subroutine of the primary therapeutic signal. A stimulation subroutine may be used to enhance concomitant pharmacotherapy, e.g., a patient being treated with VNS treatment for epilepsy may also run a stimulation subroutine that specifically modulates the safety and efficacy of concomitant antiepilepsy drugs. A subroutine may also be employed to modulate pharmacotherapy used to treat disorders distinct from those treated by the primary stimulation algorithm, e.g. a patient may be treated for depression with VNS treatment with a subroutine running to enhance the bioavailability of insulin taken for the treatment of diabetes. Thus, in some embodiments of the present invention, the electrical signal generator may provide a plurality of electrical signals to the patient to both provide a primary therapy for treatment of a first medical condition such as epilepsy, depression, bulimia, obesity, or traumatic brain injury, and a secondary therapy to modulate a concomitant drug therapy being provided to the patient. The subroutines for modulating a drug therapy may be provided during off-times of the primary therapy (i.e., during times when pulse bursts comprising the primary therapy are not being provided to the patient).

During establishment of the stimulation algorithm to be used in conjunction with administration of a selected drug, it is desirable to establish conditions in which no discomfort attributable due to the stimulation signal is experienced by the patient. If discomfort occurs, no further increase in current, pulse width, frequency, and so forth, is attempted, until the discomfort response habituates. If the discomfort does not habituate, the parameters which have been increased are decreased in steps of similar period and the patient's response is monitored accordingly. Programming, both initial and any subsequent change, is accomplished by a physician, or other trained user, employing an external programmer unit with a programming wand that is placed over the implant site of the microprocessor-containing stimulus generator. A suitable external programming unit for use with the aforementioned Model 102 signal generator is available from Cyberonics Inc., Houston, Tex. The desired therapy algorithm is programmed to set the electrical signal parameters of the electrical signal generator.

Techniques of manual and automatic activation may be employed, as described in U.S. Pat. No. 5,304,206, to activate or deactivate the electrical generator, using a sensor such as an accelerometer or a piezoelectric element mounted to the inner surface of the generator can so as to detect light taps by the patient on the implant site of the generator in the patient's body. This gives the patient limited but convenient control over the device operation, to an extent which can be determined and circumscribed by the attending physician or other appropriate caregiver. Thus, the patient may signal the device immediately upon administration of the drug to automatically or manually synchronize first, second, third, etc., electrical signals with the ingestion of the drug. It is more amenable to control that can be exercised by the patient, than other means such as an external magnet.

Therapeutic stimulating signals travel from the site of the electrode(s) at which the signals are delivered to the vagus nerve to one or more region of the brain via afferent nerve fibers, which in turn generates impulses in pathways projecting to other areas of the brain which modulate such homeostatic mechanisms at various sites in the body. In some treatment regimes, therapeutic stimulating signals travel from the stimulus site on the vagus nerve via efferent vagus nerve fibers, to an organ that affects the pharmacologic or pharmacokinetic properties of a selected drug. In other treatment regimes, both afferent and efferent stimulation pathways are employed to modulate distribution and transformation properties of the selected drug. The timing of delivery of VNS is preferably established relative to the time of administration of the selected drug or drugs. In some cases it will be desirable to synchronize VNS treatment with administration of a selected drug, while in other cases a suitable VNS signal may be applied on an "as needed" basis dependent upon when the patient experiences desired or undesired effects from the drug. In other cases, it will be desirable to employ chronic VNS treatment that is not timed to administration of a drug dose. In still other cases, it will be more efficacious to apply VNS treatment a predetermined interval of time after a drug is administered to the patient. Since an initial goal of the VNS treatment is to improve drug efficacy and reduce the dosage of the drug, some period of time may elapse after initiation of VNS treatment until an effect is observed on the underlying disorder being treated by the drug. For example, VNS treatment may be used to increase the permeability of the blood brain barrier via modulation of p-glycoproteins and thereby allow anti-neoplastic agents in particular drugs to enter the brain much easier for the treatment of tumors. An electrical signal applied to the vagus could be timed in such a manner as to allow the drug to adequately penetrate the brain, at a presumably lower and safer dose. The electrical signal for drug modulation would then be turned off at such a time that the drug has reached the brain in sufficient concentration thus restoring the permeability to pre-stimulation levels. It should be noted that the drug-modulating electrical signal may comprise a secondary therapy for the patient, and that a different electrical signal, functioning as a primary therapy for the same or a different medical condition may be allowed to continue independently of the course of drug therapy provided to the patient

EXAMPLES

Biotransformation. In one embodiment, a specific electrical signal is used to regulate hepatic function as it affects the biotransformation of a selected therapeutic drug. The vagus nerve directly projects to the liver and modulates functions such as metabolism of exogenous compounds. Modulation of liver function and, in turn, drug metabolism will impact half-life and activation of pro-drugs. A programmed electrical signal can thus be applied to a vagus nerve of the patient to enhance pharmacotherapy. In one embodiment, the electrical signal is preselected to generate efferent action potential to modulate liver function. A suitable stimulation algorithm is determined as described above, and may include monitoring changes in blood levels of the drug and its active metabolites. Changes to the electrical signal may be made based upon measured changes in blood levels of the drug, its active metabolites, or other blood parameters corresponding to the pharmacokinetic profile of the drug for the patient.

Water balance. Hypothalamic control of water balance is potentially mediated by influencing hormones such as antidiuretic hormone (ADH), Arginine Vasopressin, Oxytocin and Atrial Natriuretic Factor from the posterior pituitary gland, and may be modulated by a specific VNS electrical signal selected to influence the secretion of the foregoing hormones. Without wishing to be limited to a single theory, it is proposed that a sequence of events in neural pathways is evoked by administration of appropriate VNS, leading to a responsive release of neuropeptides or neurotransmitters into target organs involved in water metabolism and osmolality regulation, which in turn alters the pharmoacokinetic profile of selected drugs. Controlling water balance in this manner will, thereafter, impact such factors as absorption, metabolism, clearance and volume of distribution of drugs.

Alternatively, clearance and volume of distribution of a selected drug may be affected by altering the stomach's natural motility. By utilizing selected efferent stimulation algorithms, interdigestive myoelectric complexes that move through the stomach and small intestine as a result of cyclic releases of the hormone Motilin may be altered. VNS electrical signals can be programmed in ajuxtaposed fashion to the natural motility cycles to either inhibit, or slow down motility, or enhance and speed up motility in accordance with therapeutically desirable residence time of drugs in the stomach and lower intestine.

P-glycoprotein (P-gp) permeability. The permeability of the blood brain barrier may be increased by modulation of P-gp activity via VNS to ameliorate multi-drug resistance, to increase efficacy and lower the dosage of a selected drug. Multi-drug resistance poses major obstacles to effective pharmacotherapy for illnesses ranging from epilepsy to cancer. In the case of epilepsy, some data suggests that it is the inability of the pharmacotherapy to attain sufficient plasma concentrations for a therapeutic effect. P-gp is a transporter protein located on the endothelial cells of the blood brain barrier, as well as many other tissues throughout the body, and is thought to play a role in limiting the ability of drugs such as phenytoin (commonly prescribed for epilepsy) from reaching the brain. Recently an experimental, non-invasive quantitative PET imaging technique has been developed to measure P-gp activity using radio-labeled $^{11}$C-verapamil. Without being bound by theory, it is thought that such a methodology may be used to not only evaluate P-gp function in general, but also to evaluate modulation of P-gp function by vagus nerve stimulation. It may be possible by appropriately timed electrical signals applied to the vagus nerve to modulate P-gp function in such a fashion as to optimize drug delivery to target organs. P-gp is found in such regions of the body as the epithelia of the bronchi and gastrointestinal system, renal tubules of the kidney, prostate gland, the bile canaliculi and ductules, the adrenal and in endothelium of capillaries in various organs, most notably the brain, any of which may be a potential target for VNS treatment.

Synergistic Effect of VNS and Other Agents. VNS potentially acts synergistically with pharmaceutical agents to improve their effectiveness. For instance, VNS in combination with topiramate has been shown to improve alertness and behavior in children. In addition, known modes of action of VNS therapy may be used to augment the complementary known modes of action of particular drugs. For example, it is known that VNS therapy selectively modulates the noradrenergic system in a relatively acute time frame. Thus, the use of VNS therapy in conjunction with an SSRI, whose primary mode of action is serotonergic modulation, may allow a treatment regime in which both noradrenergic and serotonergic systems are modulated, to provide a more effective treatment for the patient.

Reduction of Drug Dosage. By enhancing the efficacy of a lower dose of the drug by modulating its pharmacologic and pharmacokinetic properties by VNS stimulation, the desired therapeutic effects may be obtained and the undesirable side effects may be avoided at the lower dose. Thus, where VNS may be used to modulate drug pharmacologic and/or pharmacokinetic properties, patients undergoing VNS therapy for various indications (including epilepsy) may experience a reduction of drug burden.

Increased Therapeutic Index. By suitably modulating a selected drug's pharmacologic and pharmacokinetic properties using VNS, whereby the therapeutically effective dose is reduced, the therapeutic index may be correspondingly increased as a result of providing VNS to the patient. One instance in which the lowered therapeutic index is especially desirable is the antipsychotic drug risperidone. Patients who suffer from neuropsychiatric disorders and are taking risperidone may experience deleterious symptoms because the effective dose range tends to overlap with the range at which undesirable side effects occur. Accordingly, by providing a higher effective therapeutic index, side effects experienced by the patient may be reduced.

An instance in which increasing a drug's therapeutic index is particularly desirable is in the treatment of diabetes with orally delivered insulin. The therapeutic index of insulin is relatively low. A suitable VNS stimulation signal is applied to the patient to cause insulin to retain its biological activity without provoking severe hypoglycemia within the range of the insulin administered.

Controlling drug metabolism is one way to modulate the therapeutic index and dosage. There are data to suggest that VNS modulates cytochrome P450 enzyme activity in the liver. For example, vagotomized rats have shown a decrease in P450 activity while cholinergic agents have elicited an increase in activation. The P450 system plays a key role in not only the metabolism of pharmacological agents but in the mediation of their therapeutic properties as well. Some drugs are converted into active metabolites by the P450 system. These metabolites may contribute to both the therapeutic and adverse effects. Thus management of these metabolites by stimulation of the liver via the vagus nerve may play a key role in optimizing some pharmacotherapies. For instance, bupropion is an antidepressant that is metabolized into active compounds such as hydroxybupropion, threohydrobupropion, and erythrohydrobupropion. Although the therapeutic benefit of these metabolites is uncertain, they are indeed biologically active compounds that accumulate in the body to a much greater extent than bupropion. Even small fluctuations in bupropion dose may greatly increase the concentration of the active metabolites, hence the narrow therapeutic window, i.e., low therapeutic index. It is thought that the high concentrations of these metabolites contribute to the low therapeutic index, i.e., since much of the parent drug is metabolized, a high concentration is needed for therapeutic effect, resulting in an increased risk of adverse events. Decreasing the activity of P450 enzymes by vagus nerve stimulation would decrease the metabolism of bupropion thereby increasing the therapeutic index and decreasing the therapeutic dose.

Although a best mode of practicing the invention has been described herein with reference to certain preferred embodiments and methods of treating pain, it will be understood by those skilled in the field from a consideration of the foregoing disclosure, that variations and modifications of the described embodiments and methods may be made without departing from the true spirit and scope of the invention. Accordingly, it is intended that the invention shall be limited only to the extent required by the appended claims and the rules and principles of applicable law.

What is claimed is:

1. A method of treating a patient undergoing pharmacotherapy with a selected drug for treatment of a medical disorder, the method comprising:
    administering the selected drug to said patient at a first time point to treat said medical disorder; and
    applying a first electrical signal to a vagus nerve of the patient at a second time point,
    wherein said first electrical signal is selected so as to modulate at least one pharmacologic and/or pharmacokinetic property of the selected drug in the body of the patient, wherein said at least one property is selected from the group consisting of the rate of intestinal absorption of said drug or a biologically active metabolite thereof, plasma binding of said drug, solubility of said drug in a body fluid, volume of distribution of said drug, and clearance of said drug, and
    wherein said second time point is selected from the group consisting of a selected time before said first time point, a selected time after said first time point, and a selected time in the patient's circadian rhythm after said first time point.

2. The method of claim 1, wherein administering said drug to the patient comprises administering a therapeutically effective reduced dosage of said drug compared to the dosage that would be administered to the patient in the absence of applying said first electrical signal to said vagus nerve.

3. The method of claim 1, wherein said modulating results in an increased therapeutic index of said drug.

4. The method of claim 1, wherein applying said first electrical signal to said vagus nerve comprises applying said first signal to a vagus nerve site in the cervical region of the patient.

5. The method of claim 1, wherein applying said first electrical signal to said vagus nerve comprises applying said first signal to at least one site on said vagus nerve in the supra-diaphragmatic thoracic region of the patient.

6. The method of claim 1, wherein applying said first electrical signal to said vagus nerve comprises applying said first signal to at least one site on said vagus nerve in the sub-diaphragmatic abdominal region of the patient.

7. The method of claim 1, wherein administering said drug to said patient comprises administering said drug immediately before applying said first electrical signal to said vagus nerve.

8. The method of claim 1, wherein said second time point is a predetermined interval of time after said first time point.

9. The method of claim 1, wherein administering said drug to said patient comprises chronic administration of said drug to said patient, and wherein applying said first electrical signal comprises repeatedly applying said electrical signal at a predetermined series of time intervals after said first time point.

10. The method of claim 1, wherein said method further comprises applying a second electrical signal, different from said first electrical signal, to a vagus nerve of the patient, wherein said second electrical signal is selected so as to treat a medical condition of a patient independent of the effects of said drug.

11. The method of claim 1, wherein said at least one pharmacologic and/or pharmacokinetic property comprises the rate of intestinal absorption of the selected drug, or a biologically active metabolite thereof 12. The method of claim 1, wherein said at least one pharmacologic and/or pharmacokinetic property comprises a property selected from the group consisting of plasma binding of the selected drug, solubility of said drug in a body fluid, volume of distribution of said drug, and clearance of said drug.

13. The method of claim 1, wherein applying said first electrical signal to a vagus nerve comprises modulation of the hypothalamus area of the patient's brain.

14. The method of claim 1, wherein applying said first electrical signal to a vagus nerve comprises modulation of the brainstem area of the patient's brain.

15. The method of claim 1, wherein applying said first electrical signal to said vagus nerve comprises modulation of the function of an organ selected from the group consisting of the stomach, the pancreas, the liver, the lungs, the intestines, and the kidneys.

16. The method of claim 1, wherein applying said first electrical signal to said vagus nerve comprises applying said signal to a main branch of the left or right vagus nerves, or to a branch of the vagus nerve connecting a main branch of the vagus nerve to an organ selected from the group consisting of the stomach, the pancreas, the liver, the lungs, the intestines and the kidneys.

17. The method of claim 1, wherein applying said first electrical signal to said vagus nerve comprises applying said signal to an electrically conductive tissue adjacent to the vagus nerve to indirectly apply said first electrical signal to said vagus nerve.

18. A method of enhancing treatment of a patient undergoing pharmacotherapy with a predetermined dosage of a selected drug for treatment of a medical disorder, the method comprising:
   (a) administering a first predetermined dosage of said drug to the patient;
   (b) applying a first electrical signal to at least one site on a left or right vagus nerve of the patient, wherein said first electrical signal is selected so as to modulate at least one pharmacologic and/or pharmacokinetic property of the selected drug in the body of the patient, wherein said at least one property is selected from the group consisting of the rate of intestinal absorption of said drug or a biologically active metabolite thereof, plasma binding of said drug, solubility of said drug in a body fluid, volume of distribution of said drug, and clearance of said drug;
   (c) determining from the resulting modulation of said at least one property an increase or decrease in the efficacy of said drug; and
   (d) decreasing the drug dosage to enhance treatment of said patient for said disorder if the resulting modulation increases the efficacy of said drug.

19. A method of enhancing treatment of a patient undergoing therapeutic vagus nerve stimulation for a medical disorder, comprising:
   (a) applying a first electrical signal to a site on a vagus nerve of the patient, wherein said first electrical signal is selected so as to therapeutically treat said medical disorder;
   (b) administering a drug therapy to said patient for the same or a different medical disorder; and
   (c) applying a second electrical signal to a site on a vagus nerve, wherein said second electrical signal is selected to modulate at least one pharmacologic and/or pharmacokinetic property of the selected drug in the body of the patient, said at least one property being selected from the group consisting of the rate of intestinal absorption of said drug or a biologically active metabolite thereof, plasma binding of said drug, solubility of said drug in a body fluid, volume of distribution of said drug, and clearance of said drug, to enhance said drug therapy.

20. The method of claim 19, wherein said second electrical signal is applied to a site on a vagus nerve that is different from the site where said first electrical signal is applied.

21. The method of claim 19, wherein said second electrical signal is applied during off-times of said first electrical signal.

22. The method of claim 19, wherein applying said second electrical signal causes enhancement of at least one of bioavailability, efficacy and safety of said drug.

23. The method of claim 19, wherein said first electrical signal, said drug, and said second electrical signal are selected to synergistically enhance treatment of said medical disorder.

* * * * *